United States Patent [19]

Hogan

[11] Patent Number: 4,584,881

[45] Date of Patent: Apr. 29, 1986

[54] WELD TESTING HEAD

[75] Inventor: Joseph Hogan, South Bend, Ind.

[73] Assignee: Mac Engineering and Equipment Company, Inc., Benton Harbor, Mich.

[21] Appl. No.: 621,118

[22] Filed: Jun. 15, 1984

[51] Int. Cl.$^4$ .............................................. G01N 3/24
[52] U.S. Cl. ...................................................... 73/842
[58] Field of Search ......................... 73/842, 845, 846; 29/407, 593 (U.S. only)

[56] References Cited

U.S. PATENT DOCUMENTS

| | | | |
|---|---|---|---|
| 2,261,783 | 11/1941 | Stull | 73/842 |
| 2,453,576 | 11/1948 | Jacob | 73/845 |
| 4,012,947 | 3/1977 | Tiegel | 73/842 |

Primary Examiner—Stewart J. Levy
Assistant Examiner—Robert R. Raevis
Attorney, Agent, or Firm—Michael, Best & Friedrich

[57] ABSTRACT

Disclosed herein is apparatus for testing the weld strength of a battery connection extending through a hole in a battery partition and between first and second lugs located in adjacent parallel relation to the partition and each including an end surface and a pair of side surfaces extending in parallel relation to each other and in transverse relation to the end surface, which apparatus comprises a vertically movable main frame including a holding surface adapted for engagement with the end surface of the first lug, a sub-frame carried by the main frame and movable vertically relative to the main frame, horizontally movable clamping members carried by the sub-frame for clampingly engaging the side surfaces of the second lug to the sub-frame, a cylinder for applying a force for vertically displacing the main frame to engage the holding surface with the end surface of the first lug and to retain the holding surface against vertical movement after engagement with the end surface of the first lug, a second cylinder for applying a force for horizontally displacing the clamping members to clampingly engage the second lug to the sub-frame, and a third cylinder for applying a force for vertically upwardly displacing the sub-frame while maintaining the sub-frame in clamping engagement with the second lug and while maintaining the holding surface in engagement with the end surface of the first lug and against vertical movement, whereby to subject the connection to shearing stress.

2 Claims, 4 Drawing Figures

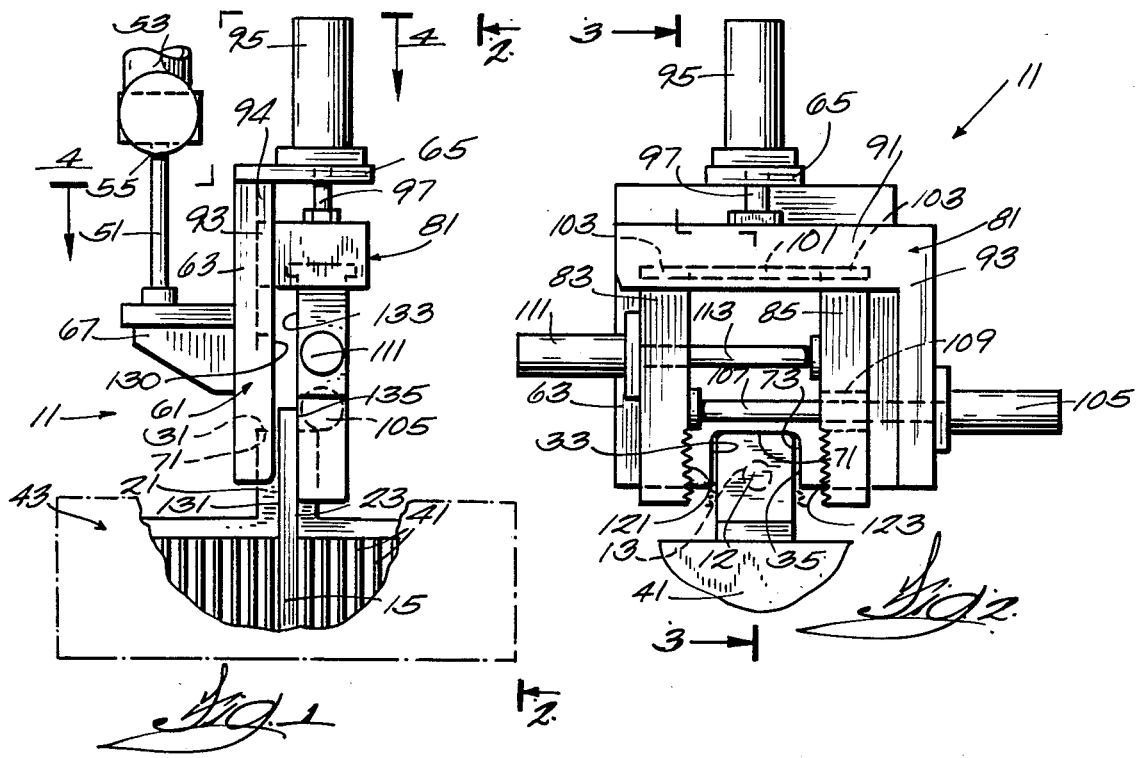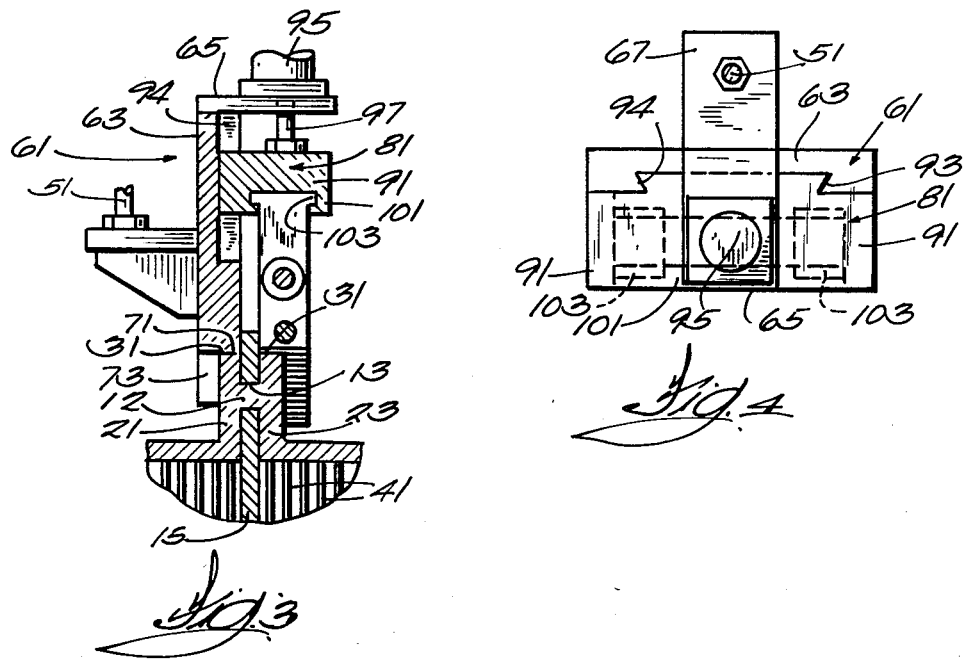

WELD TESTING HEAD

BACKGROUND OF THE INVENTION

The invention relates generally to devices for testing the strength of a weld extending through a partition in a battery case and connecting opposed lugs located on opposite sides of the battery case.

Attention is directed to the U.S. Tiegel Pat. No. 4,012,947 issued Mar. 22, 1977 which discloses an arrangement for testing battery welds, which arrangement is limited to applying horizontally directed forces to the opposed side surfaces of the opposed lugs. In the Tiegel arrangement, the forces applied for testing are directed along the horizontal extent of the partition and, on occasions, can subject the partition to twisting and deformation. By comparison, in the construction disclosed hereinafter, the weld connection can be tested by application of opposed vertically directed forces, thereby limiting possible twisting or deformation of the partition.

SUMMARY OF THE INVENTION

The invention provides apparatus for testing the weld strength of a battery connection extending through a hole in a battery partition and between first and second lugs located in adjacent parallel relation to the partition and each including an end surface and a pair of side surfaces extending in parallel relation to each other and in transverse relation to the end surface, which apparatus comprises a vertically movable main frame including a holding surface adapted for engagement with the end surface of the first lug and for retaining the end surface of the first lug against vertical movement, a sub-frame carried by the main frame and movable vertically relative to the main frame, means carried by the sub-frame and including at least one horizontally movable member for clampingly engaging the side surfaces of the second lug to the sub-frame, means for applying a force for horizontally displacing the clamping member to clampingly engage the second lug to the sub-frame, and means for applying a force for vertically upwardly displacing the sub-frame while maintaining the sub-frame in clamping engagement with the second lug and while maintaining the end surface of the first lug against vertical movement, whereby to subject the connection to shearing stress.

The invention also provides apparatus for testing the weld strength of a battery connection extending through a hole in a battery partition and between first and second lugs located in adjacent parallel relation to the partition and each including an end surface and a pair of side surfaces extending in parallel relation to each other and in transverse relation to the end surface, which apparatus comprises a vertically movable main frame including a holding surface adapted for engagement with the end surface of the first lug, a sub-frame carried by the main frame and movable vertically relative to the main frame, a first clamping member carried by the sub-frame and movable horizontally relative thereto and into engagement with one of the side surfaces of the second lug, a second clamping member carried by the sub-frame for horizontal movement relative thereto and relative to the first clamping member and into clamping engagement with the other of the side surfaces of the second lug so as to clampingly engage the lug therebetween, means for applying a force directed to displace the main frame vertically to engage the holding surface with the end surface of the first lug and to retain the holding surface against vertical movement after engagement with the end surface of the first lug, means for applying a force directed to horizontally displace the clamping members relative to each other to clampingly engage therebetween the second lug, and means for applying a force directed to displace the sub-frame vertically upwardly while maintaining the first and second clamping members in clamping engagement with the second lug and while maintaining the holding surface in engagement with the end surface of the first lug and against vertical movement, whereby to subject the connection to shearing stress.

Other features and advantages of the invention will become known by reference to the following general description, claims and appended drawings.

THE DRAWINGS

FIG. 1 is a partially schematic side elevation view of one embodiment of a weld-testing apparatus embodying various features of the invention.

FIG. 2 is a side elevational view taken generally along line 2—2 of FIG. 1.

FIG. 3 is a sectional view taken generally along line 3—3 of FIG. 2, and

FIG. 4 is a sectional view taken generally along line 4—4 of FIG. 1.

Before explaining one embodiment of the invention in detail, it is to be understood that the invention is not limited in its application to the details of construction and the arrangement of components set forth in the following description or illustrated in the drawings. The invention is capable of other embodiments and of being practiced and carried out in various ways. Also, it is to be understood that the phraseology and terminology employed herein is for the purpose of description and should not be regarded as limiting.

GENERAL DESCRIPTION

Shown in FIG. 1 is a device or apparatus 11 for testing the strength of a welded connection 12 (see FIG. 2) which extends through an opening or aperture 13 in an interior battery partition or wall 15 and which electrically connects two spaced lugs 21 and 23 which extend in parallel relation to each other and in adjacent parallel relation to the opposite sides of the partition 15. Each of the lugs 21 and 23 includes, see FIG. 3, an upper or outer end or edge 31 and, see FIG. 2, a pair of side or vertical edges 33 and 35 which extend in generally parallel relation to each other and in generally perpendicular relation to the outer edge or end 31. In turn, the lugs 21 and 23 are connected to battery plates 41 and the entire assembly is located within an upwardly open battery case 43, shown schematically.

The testing device 11 is adapted to be carried by a generally automatic machine (not shown) having a tool head 51 capable of selective vertical and horizontal movement. In the drawings, the tool head 51 is shown schematically as a vertical member. Suitably connected to the member 51, interiorly of the automatic machine, are first and second (schematically illustrated) fluid cylinders 53 and 55 for moving the head 51 in two directions which are perpendicular to each other, i.e., for example, vertically and horizontally.

Connected to the head 51 for such vertical and horizontal movement is a main frame 61 which, as shown in FIG. 1, is generally of L-shape construction, including a vertical leg or member 63 and a horizontal leg or member 65. The vertical leg or member 63 is connected to the head 51 by a bracket 67 which extends fixedly from the vertical leg or member 63 and is removably attached to the head 51 in any suitable fashion.

The vertical leg or member 63 includes an abutment surface 71 which, in response to suitable movement of the head 51 relative to the battery case 43, is adapted to engage the outer or top end 31 of the lug 21. While other constructions can be employed, in the illustrated construction, the surface 71 constitutes the upper surface of a downwardly open recess 73 adapted to partially telescopically enclose the lug 21 in response to vertical movement which engages the surface 71 with the outer end 31 of the lug 21.

Carried on the main frame 61 for vertical movement relative thereto is a sub-frame 81. In turn, the sub-frame 81 carries means including at least one horizontally movable member for clampingly engaging the sides 33 and 35 of the lug 23, thereby clamping the lug 23 to the sub-frame 81. While other constructions can be employed, in the illustrated construction, such clamping means comprises a pair of clamping jaws of members 83 and 85 which are adapted to clampingly engage the sides 33 and 35 of the lug 23. While other arrangements can be employed, such as movably displacing only one of the clamping members 83 and 85, in the illustrated construction, the clamping members 83 and 85 are both horizontally movable relative to each other and relative to the sub-frame 81.

More particularly, the sub-frame 81 is also of L-shaped construction and includes an upper horizontally extending cross bar or beam 91 and a leg or member 93 fixedly extending downwardly from the upper cross bar or beam 91.

Means are provided for guiding vertical movement of the sub-frame 81 relative to the main frame 61. While various arrangements can be employed, in the illustrated construction, such means comprises a pair of guides or ways 93 provided on the cross beam 91 and a mating pair of guides or ways 94 provided on the vertical leg 63 of the main frame 61.

Means are also provided for selectively displacing the sub-frame 81 vertically relative to the main frame 61. While various arrangements can be employed, in the illustrated construction, such means is provided by a fluid cylinder 95 which extends fixedly from the main frame 61 and which includes a piston rod 97 fixedly connected to the sub-frame 81. Accordingly, fluid actuated movement of the piston (not shown) within this cylinder 95 causes vertical extension and retraction of the cross bar 91 relative to the main frame 61. Any suitable means can be provided for controllably supplying pressure fluid to the cylinder 95.

Means are provided for guiding the jaws 83 and 85 for horizontal movement relative to the cross beam 91. While various arrangements can be employed, in the illustrated construction, such means comprises ways or guides 101 extending horizontally on the cross beam 91 and mating ways or guides 103 on each of the vertically extending jaws 83 and 85.

Means are provided for displacing the jaws 83 and 85 horizontally relative to the cross bar 91. While various arrangements can be employed, in the illustrated construction, such means comprises a first fluid cylinder 105 which is fixed to the vertical leg 93 of the sub-frame 81 and which includes a piston rod 107 which extends through a clearance hole 109 in th jaw 85 and which is fixed to the jaw 83. Accordingly, fluid actuated movement of the piston (not shown) within the cylinder 105 can extend and retract the jaw 83 relative to the vertical leg 87 of the sub-frame 81.

Means are also provided for displacing the other jaw 85 relative to the first jaw 83 in the horizontal direction. While other arrangements can be employed, in the illustrated construction, such means comprises a second fluid cylinder 111 mounted on the first jaw 83 and including a piston rod 113 which is fixedly connected to the second jaw 85. Accordingly, fluid actuated movement of the piston (not shown) within the second cylinder 111 causes extension and retraction of the second jaw 85 relative to the first jaw 83.

Any suitable means can be provided for controllably supplying pressure fluid to the cylinders 105 and 111.

The jaws 83 and 85 respectively include clamping surfaces 121 and 123 which are preferably serrated to minimize relative movement between the jaws 83 and 85 and the lug 23 when the jaws or clamps 83 and 85 are tightly engaged with the side edges 33 and 35 of the lug 23.

The ways 93, 94 and 101, 103 on the main frame 61 and on the sub-frame 81 and on the clamping jaws or members 83 and 85 are arranged so that, when the side surface 130 of the main frame vertical leg 63 is against one side 131 of the partition 15, the side surfaces 133 of the clamping jaws or members 83 and 85 are located adjacent the other side 135 of the partition 15.

In operation, the main frame 61 is first horizontally positioned so as to locate the side surface 130 of the vertical leg 63 of the main frame 61 adjacent to the partition 15. The main frame 61 is then vertically displaced to engage the abutment surface 71 with the outer end 31 of the lug 21.

Next the cylinder 105 is actuated to engage the clamping surface 121 with the side or edge 33 of the lug 23. Subsequently, the cylinder 111 is actuated to engage the clamping surface 123 with the other side edge 35 of the lug 23 with sufficient pressure to tightly clamp the lug 23 between the clamping jaws 83 and 85.

With the outer end 31 of the lug 21 engaged by the surface 71 of the main frame 61, whichsurface 71 acts as a stop, and while the clamping jaws 83 and 85 are tightly clamped to the lug 23, the cylinder 95 is then actuated to lift the sub-frame 81 with a predetermined force sufficient to test the strength of the weld extending through the partition of wall 15. If the weld is of good quality, the force exerted by the cylinder 95 will be insufficient to raise the sub-frame 81 any appreciable amount. If the weld is of poor quality, the force exerted by the cylinder 95 will be sufficient to cause upward displacement of the sub-frame 81 and clamping jaws 83 and 85, thus rupturing the poor weld and thus signifying that the weld was of poor condition.

Various features of the invention are set forth in the following claims.

I claim:

1. Apparatus for testing the weld strength of a battery connection extending through a hole in a battery partition and between first and second lugs located in adjacent parallel relation to the partition and each including an end surface and a pair of side surfaces extending in parallel relation to each other and in transverse relation to the end surface, said apparatus comprising a vertically movable main frame including a holding surface adapted for engagement with the end surface of the first lug and for retaining the end surface of the first lug against vertical movement, a sub-frame carried by said main frame and movable vertically relative to said main frame, means carried by the sub-frame and including at least one horizontally movable member for clampingly engaging the side surfaces of the second lug to said sub-frame, means for applying a force for horizontally displacing said clamping member to clampingly engage the second lug to said sub-frame, and means for applying a force for vertically upwardly displacing said sub-frame while maintaining said sub-frame in clamping engagement with the second lug and while maintaining the end surface of the first lug against vertical movement, whereby to subject the connection to shearing stress.

2. Apparatus for testing the weld strength of a battery connection extending through a hole in a battery partition and between first and second lugs located in adjacent parallel relation to the partition and each including an end surface and a pair of said surfaces extending in parallel relation to each other and in transverse relation to the end surface, said apparatus comprising a vertically movable main frame including a holding surface adapted for engagement with the end surface of the first lug, a sub-frame carried by said main frame and movable vertically relative to said main frame, a first clamping member carried by said sub-frame and movable horizontally relative thereto and into engagement with one of the side surfaces of the second lug, a second clamping member carried by said sub-frame for horizontal movement relative thereto and relative to said first clamping member and into clamping engagement with the other of the side surfaces of the second lug so as to clampingly engage the lug therebetween, means for applying a force directed to displace said main frame vertically to engage said holding surface with the end surface of the first lug and to retain said holding surface against vertical movement after engagement with the end surface of the first lug, means for applying a force directed to horizontally displace said clamping members relative to each other to clampingly engage therebetween the second lug, and means for applying a force directed to displace said sub-frame vertically upwardly while maintaining said first and second clamping members in clamping engagement with the second lug and while maintaining said holding surface in engagement with the end surface of the first lug and against vertical movement, whereby to subject the connection to shearing stress.

* * * * *